United States Patent [19]
Farstad

[11] 4,085,349
[45] Apr. 18, 1978

[54] PIEZO ELECTRIC TRANSDUCER FOR MEASURING INSTANTANEOUS VIBRATION VELOCITY

[75] Inventor: Johan T. Farstad, Sunbury, Ohio

[73] Assignee: IRD Mechanalysis, Inc., Columbus, Ohio

[21] Appl. No.: 666,355

[22] Filed: Mar. 12, 1976

[51] Int. Cl.² ........................................... H01L 41/04
[52] U.S. Cl. ............................... 310/319; 73/517 R; 310/329
[58] Field of Search .......... 310/8.4; 73/516 R, 517 R, 73/517 RV, 518

[56] References Cited

U.S. PATENT DOCUMENTS

| Re. 28,596 | 10/1975 | Siegel | 310/8.4 X |
|---|---|---|---|
| 3,285,074 | 11/1966 | Elazar | 310/8.4 X |
| 3,356,868 | 12/1967 | Cother | 310/8.4 |
| 3,389,276 | 6/1968 | Gradin et al. | 310/8.4 |
| 3,390,286 | 6/1968 | Gradin et al. | 310/8.4 |
| 3,453,457 | 7/1969 | Hayer et al. | 310/8.4 |
| 3,749,946 | 7/1973 | Ruti | 310/8.4 X |

*Primary Examiner*—Mark O. Budd
*Attorney, Agent, or Firm*—Harry B. Keck; George E. Manias

[57] ABSTRACT

A piezo electric transducer employs a stack of piezo electric crystals interposed between electrodes and maintained under compression to develop an electrical charge which instantaneously corresponds to the acceleration of the device. One or two electrical resistors in series with the piezo electric crystal stack output develops a charge which instantaneously corresponds to the velocity of the device. The velocity responsive charge is delivered to a charge converter which may be located remotely from the piezo electric transducer. The charge converter generates an electrical signal having a voltage which is proportional to the instantaneous velocity of the device. The assembly permits use of high-sensitivity piezo electric crystals.

3 Claims, 9 Drawing Figures

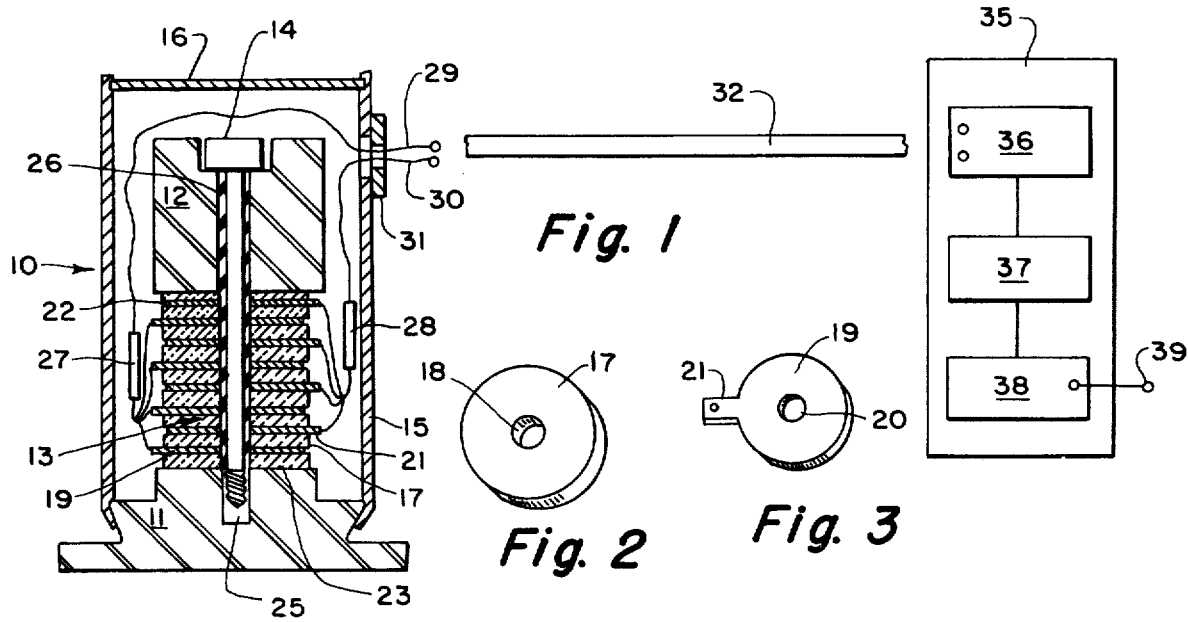
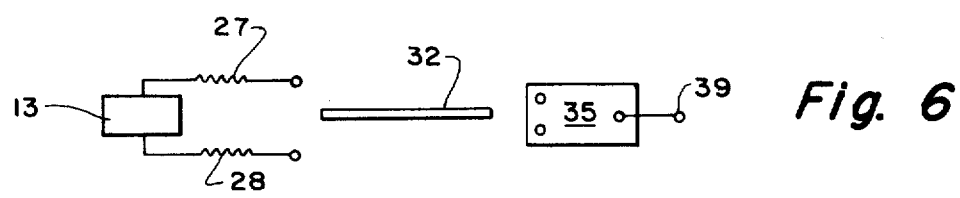
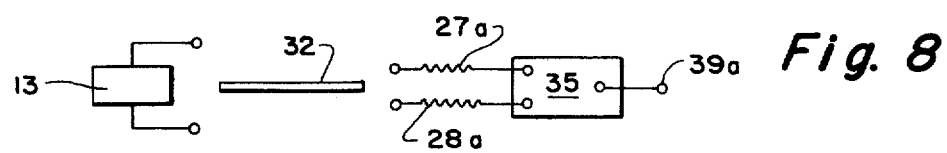
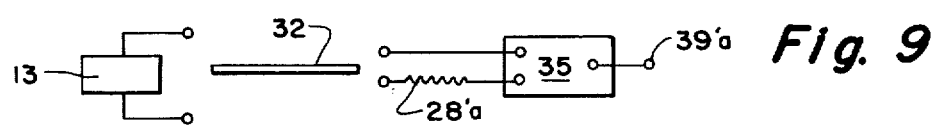

PIEZO ELECTRIC TRANSDUCER FOR MEASURING INSTANTANEOUS VIBRATION VELOCITY

BACKGROUND OF THE INVENTION

1. Field of the Invention

This invention relates to piezo electric transducers for generating an electrical signal related to the instantaneous velocity of the transducer.

2. Description of the Prior Art

Velocity responsive electromagnetic transducers of the seismic variety are widely used in vibration analysis. See U.S. Pat. No. 3,157,852. Velocity responsive eddy current devices also are employed to measure instantaneous velocity of vibrating bodies. See U.S. Pat. Nos. 3,521,158; 3,521,159. Such velocity responsive devices have limited sensitivity at vibration frequencies below ten cycles per second and above one thousand cycles per second.

Prior art accelerometer devices employing compressed piezo electric crystals have been employed to measure the instantaneous acceleration of a vibrating body. The prior art piezo electric crystal accelerometers develop an electrical charge which is proportional to the instantaneous acceleration. Such accelerometer installations are limited to low-sensitivity piezo electric crystals, e.g., sensitivities below 1,000 pico-coulombs per g. The instantaneous acceleration responsive electric charge is delivered by cable to a remote monitoring circuit for indicating the instantaneous acceleration by converting the "charge+ to a corresponding voltage. The limitation of sensitivity results from the fact that the more sensitive piezo electric crystals have a low natural frequency which tends to be excited in the crystal acceleration mode to yield a large output signal which saturates the charge amplifier. Thus to avoid amplifier saturation, the less sensitive piezo electric crystals have been employed, e.g., crystals having sensitivities of the order of 10 to 100 pico-coulombs per g.

SUMMARY OF THE INVENTION

According to the present invention a high-sensitivity piezo electric crystal stack with interposed electrodes is compressed between a base and a seismic mass. Alternate electrodes are connected in parallel with each other and in series with one or two electrical resistors to develop an output electrical charge which is proportional to the instantaneous velocity of the transducer. High sensitivity piezo electric crystal devices are employed in this installation, i.e., crystals having a sensitivity greater than 1,000 pico-coulombs per g. Preferably the devices have a sensitivity of 5,000 to 10,000 pico-coulombs per g. The high-sensitivity piezo electric crystals may be employed in the present assembly because the instantaneous velocity of the transducer is relatively low at the natural frequency of the crystals. The output electrical charge from the present transducer is preferably applied to a cable for delivery to a remote monitoring circuit. Inasmuch as cable capacitance is not a factor in the system output, cable length is not a practical limiting factor. Cables up to 1,000 feet may be employed. The cable delivers the electrical charge into a charge converter which develops an electrical voltage corresponding to the instantaneous velocity of the transducer.

As an alternative embodiment, the resistor or resistors may be applied to the system adjacent to the charge amplifier and remote from the transducer.

The resulting transducer is useful in measuring instantaneous velocities over a relatively wide range of velocities from about one cycle per second through about 4,000 cycles per second with an acceptable accuracy.

BRIEF DESCRIPTION OF THE DRAWINGS

FIG. 1 is a partly cross-sectional, partly schematic illustration of the present transducer showing the actual transducer in cross-section and the connecting cable and circuitry schematically.

FIG. 2 is a perspective illustration of a typical doughnut-shaped piezo electric crystal.

FIG. 3 is a schematic illustration of a doughnut-shaped electrode.

FIGS. 6, 7, 8 and 9 are schematic illustrations of four alternative embodiments of the present invention.

DESCRIPTION OF THE PREFERRED EMBODIMENT(S)

Figure 4:
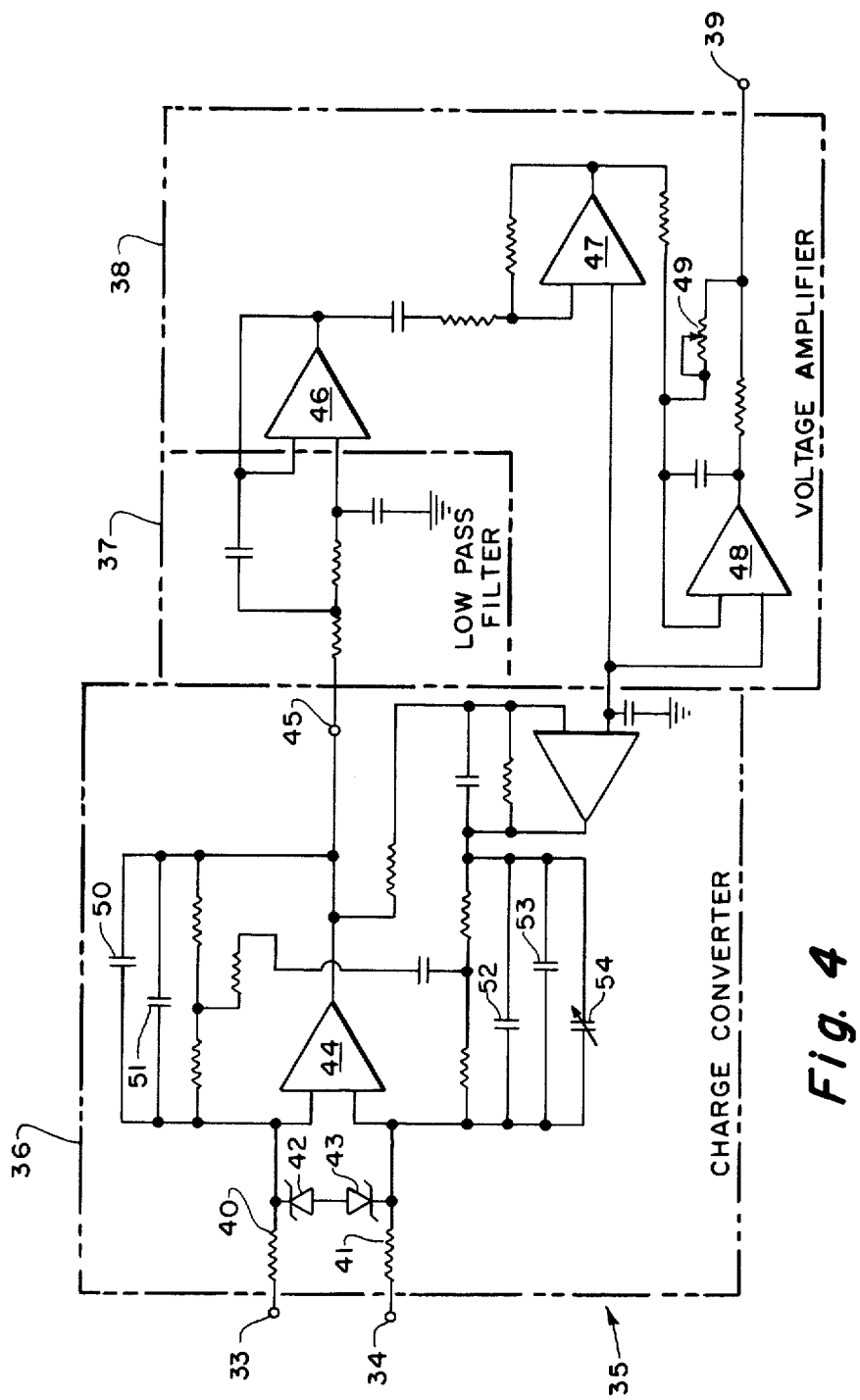
FIG. 4 is a schematic illustration of typical circuitry useful in combination with the present transducer.

Vibration transducers are employed in a variety of installations. They may be employed in unbalance analysis of rotating bodies; vibration measurements both repetitive and transient; continuous monitoring of instantaneous vibrations. Such installations require an electromechanical transducer of some type which can generate an electrical signal responsive to the instantaneous mechanical vibration of the body under inspection. Seismic transducers are securely mounted so as to move in unison with the body under inspection. The transducer is customarily connected by an electrical conductor to a conversion circuit which receives an electrical signal and generates a useful result in the form of a meter reading, a visible manifestation on an oscilloscope or similar read-out device; an alarm signal such as a lamp illumination or an audible sound when the observed vibration exceeds pre-established threshold levels; circuit opening devices for terminating further activity when observed vibrations exceed pre-established threshold levels; and the like.

In its preferred embodiment the present transducer 10 comprises a cannister device as shown in FIG. 1 including a circular base 11, a seismic mass 12, a piezo electric crystal stack 13, a connecting tension bolt 14, all secured within a cylindrical casing 15 and cover cap 16. The piezo electric crystal stack 13 includes alternating piezo electric crystals 17 (see FIG. 2) having a central bore 18 and electrodes 19 (see FIG. 3) having a central bore 20 and a radial connector tab 21. Shown in FIG. 1 are seven piezo electric crystal elements 17 and eight electrodes 19. A mica doughnut-shaped disc 22 is applied to the top of the uppermost electrode 19 to insulate that uppermost electrode from the seismic mass 12. Another mica disc 23 is applied beneath the bottom electrode 19 to insulate that bottom electrode from the base 11.

The base 11 and the seismic mass 12 are fabricated from non-magnetic steel, e.g., austenite stainless steel. The seismic mass 12 has a central clearance bore 24 for receiving the tension bolt 14. The base 11 has a central, internally threaded well 25 for receiving the threaded end of the tension bolt 14. A suitable insulating plastic sleeve 26 is applied over the body of the tension bolt 14 where it passes through the central bores 18, 20 of the crystals 17, 19, respectively. The plastic sleeve 26 preferably is a shrink fit plastic, such as Teflon. The tension bolt 14 is tightened until a compressive stress on the piezo electric crystals of the order of 2000 to 4000 psi is achieved. The crystals 17 should be maintained in a preloaded state at the highest anticipated acceleration exposure.

The piezo electric crystal elements 17 are ceramic materials having piezo electric properties, for example, lead-zirconate-titanate crystals are suitable. The seismic mass 12 in a typical unit weighs about one pound in order to achieve a desirably high sensitivity in the unit. The base member 11 should be sufficiently large to provide adequate rigid mounting to the body under inspection.

It will be observed from FIG. 1 that four of the electrode tabs are connected by conductors to a resistor 27 and the other four alternating electrode tabs are connected by conductors to another resistor 28. The resistors 27, 28 are connected to output conductors 29, 30 which extend through an aperture 31 in the cylindrical casing 15.

It will be observed that the cover cap 16 is fitted into shoulders at the upper edges of the cylindrical casing 15 and the outer top portions of the cylindrical casing 15 are rolled over the perimeter of the cover plate 16. Similarly the base member 11 has a circular shoulder which engages an internal shoulder in the bottom of the casing 15 and the outer surface of the casing 15 is rolled into an undercut portion of the base member 11 to provide a tamperresistant seal for the unit.

While the resistors 27, 28 appear to be unsupported, it is preferred that they be secured by an adhesive to the base member 11 to prevent vibration of the resistors and conductors.

The two conductors 29, 30 are connected to a cable 32 and ultimately to the input terminals 33, 34 of a conversion circuit 35 which includes a differential charge converter 36, a low pass filter 36 and a voltage amplifier 38 which produces an output signal at a terminal 39.

The conversion circuitry is illustrated in more detail in FIG. 4 wherein the differential charge converter is equipped with a high voltage input protection circuit including a pair of resistors 40, 41 and a pair of back-to-back Zener diodes 42, 43. The signal applied to the terminals 33, 34 is a velocity responsive electrical charge related to the instantaneous velocity of the transducer 10 (FIG. 1). The velocity responsive electrical charge is applied to the input terminals of an integrated circuit 44 operating as a charge converter to produce an output signal at the terminal 45 which is an electrical voltage related to the instantaneous velocity of the transducer. The integrated circuit 44 operates as a high gain amplifier with negative capacitance feedback. The voltage of the terminal 45 is delivered through a low pass filter 37 and delivered to the input terminals of an operational amplifier 46, another operational amplifier 47 and a third operational amplifier 48 for delivery to the output terminal 39. A potentiometer 49 permits adjustment of the level of output voltage at the output terminal 39.

It will be observed in connection with the differential charge converter integrated circuit 44 that two parallel capacitors 50, 51 are balanced against three parallel capacitors 52, 53, 54 to permit accurate balancing of the charge converter circuit 36. One of the capacitors 54 is a variable capacitor to permit trim adjustments to accommodate manufacturing tolerances of the circuit components.

OPERATION OF THE PRESENT TRANSDUCER

Figure 5:
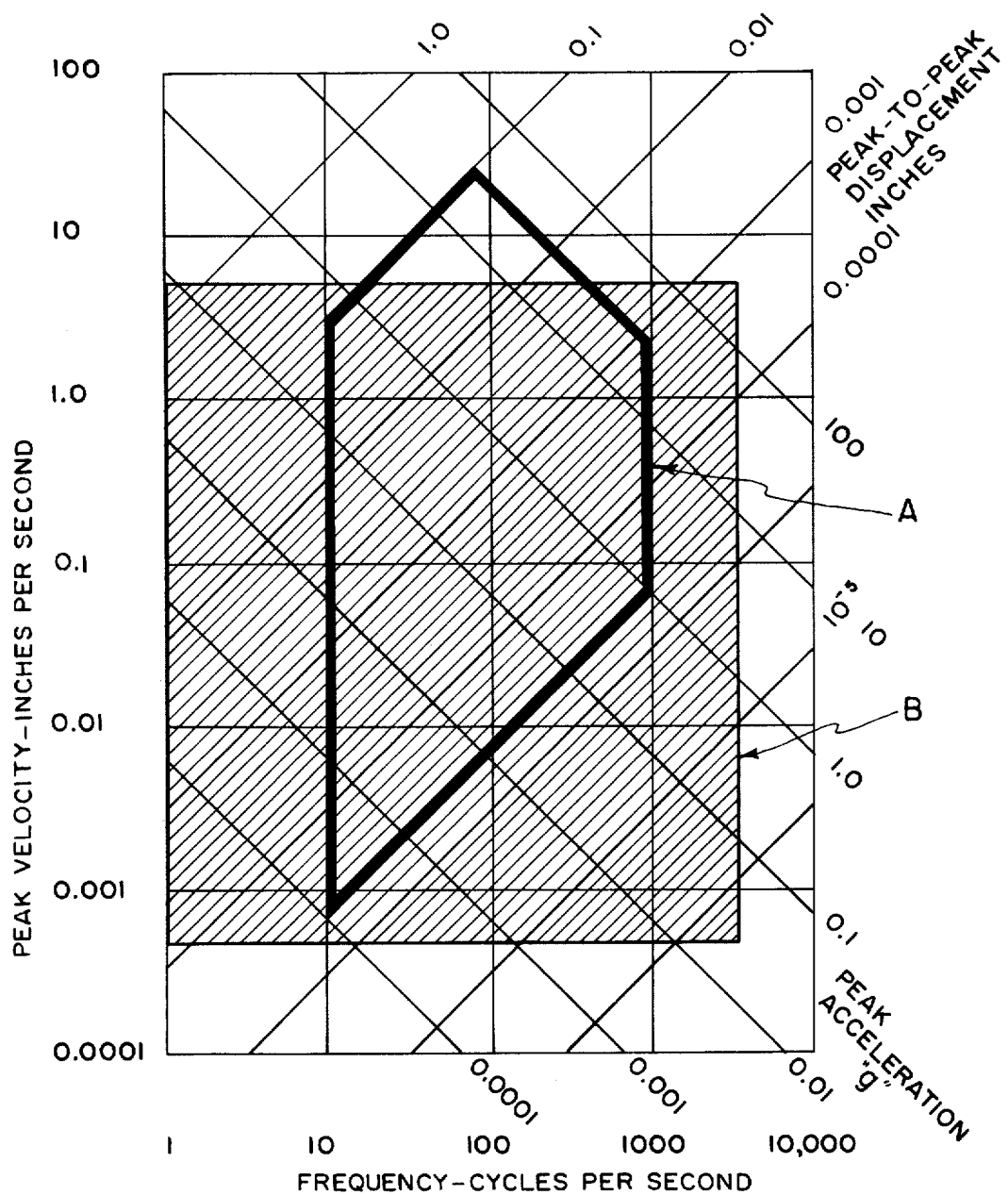
FIG. 5 is a graphical illustration showing the range of the present transducer and the range of prior art velocity responsive vibration transducers.

FIG. 5 illustrates graphically the relationship between the frequnecy of repetitive vibrations (in cycles per second) and the amplitude of vibration (in inches per second). FIG. 5 shows a range of frequencies from one cycle per second through 10,000 cycles per second and a corresponding range of vibration amplitude from 100 inches per second through 0.0001 inch per second. Plotted on FIG. 5 at 45° angle in a positive direction are the corresponding peak-to-peak vibration displacements ranging from 1.0 inch through $10^{-5}$ inch. Also plotted in FIG. 5 are the corresponding peak acceleration values ranging from 100 g through 0.0001 g.

Within the graphical framework of FIG. 5 there is a bold-line bordered area A which establishes the approximate limitations of existing velocity responsive transducers. They are limited to frequency ranges between 10 cycles per second and about 1,000 cycles per second. They are further limited by the peak-to-peak displacement of the vibrating body from a range of about 0.1 inch to about 0.00005 inch. They are further limited to accelerations below about 20 g.

The accelerometer device of the present invention appears to be useful over the shaded area B of FIG. 5. Acceptable frequency ranges from one through 4,000 cycles per second and over velocities from about 0.0005 through about 5 inches per second. The device is particularly useful in the low frequency ranges from about one through about 10 cycles per second.

Actual tests of the device have indicated the following characteristics. The device has a sensitivity of approximately 30 pico-coulombs per inch per second when measuring velocity. This corresponds to an acceleration sensitivity of approximately 5,000 pico-coulombs per g. The device has a natural frequency much higher than 10,000 cycles per second which indicates that the device at all times is functioning well below its resonance.

The device has been tested with a spectrum of frequencies and shows 92 percent response at one cycle per second, 100 percent response at four cycles per second and 95 percent response at 4,000 cycles per second. The device can be operated at temperatures up to about 500° F without damage.

The device exhibits only a 10% phase shift at 5 cycles per second; 3% at 10 c.p.s.; and negligible above 20 c.p.s. This negligible phase shift permits the device to be used as a balancing transducer if required.

Alternative Embodiments

As illustrated in FIG. 6 the preferred device employs two resistors 27, 28 and a differential charge converter 36. It is feasible, as in FIG. 7, to employ a single resistor 28' and a single ended charge converter in the conversion circuit 35' to generate an output signal at terminal 39'.

The equation for operation of the piezo electric devices of FIGS. 6 and 7 is:

$$Q_o = Q_i \left( \frac{1}{j2\pi fCR + 1} \right)$$

wherein $Q_o$ is the transducer output charge;

$Q_i$ is the charge generated in the piezo electric crystals;

R is the series resistance;

C is the capacitance of the crystal;

$f$ is the frequency (in cycles/second).

The resistance value R in the foregoing equation for the preferred embodiment of FIG. 6 is the sum of the resistance of resistors 27, 28. In the alternative embodiment of FIG. 7, the resistance value R is the resistance of the single resistor 28'.

By adjusting the value of R in the above equation, the low frequency response and the sensitivity of the transducer can be varied. For example, if R is doubled, the lower limit of useful frequency is halved, but the sensitivity also is halved. The present system permits the use of transducers having a sensitivity of 1000 picocoulombs/g and higher.

As shown in FIG. 8, the piezo electric crystal 13 has its terminals connected directly to the cable 32 which is joined to the input terminal of the charge amplifier 35 through two resistors 27a, 28a. In FIG. 9, only a single resistor 28a' is provided between the cable 32 and the charge amplifier 35'. The resulting output signal for both FIGS. 8 and 9 is determined by the equation $$Q_o = Q_i \left[ \frac{1}{j\omega (C_1 + C_2) R + 1} \right]$$

wherein $C_2$ is the capacitance of the cable 32;

R is the resistance (of 27a and 28a in FIG. 8; of 28a' in FIG. 9); and the other factors have the same meaning as hereinbefore assigned.

I claim:

1. A transducer for measuring velocity of vibrating bodies including:
    an enclosure containing a piezo electric element maintained under compression between two seismic masses, one of said seismic masses being rigidly attached to the body under observation;
    a pair of electrical conductors, each leading from said piezo electric element through a series resistor to an output terminal;
    a cable connecting the said output terminals to the input terminals of a different charge converter, said charge converter being adapted to convert an electric charge into an alternating voltage having an amplitude corresponding to the instantaneous velocity of the body under observation.

2. The transducer of claim 1 wherein the piezo electric element has a sensitivity greater than 1000 picocoulombs/g.

3. The transducer of claim 1 wherein a high voltage protection circuit is interposed between the said cable and the said input terminal of the said charge converter.

* * * * *